United States Patent
Otsubo et al.

(10) Patent No.: US 9,035,125 B2
(45) Date of Patent: May 19, 2015

(54) DISPOSABLE WEARING ARTICLE

(75) Inventors: Toshifumi Otsubo, Kagawa (JP);
Tatsuya Hashimoto, Kagawa (JP);
Mariko Takeuchi, Kagawa (JP)

(73) Assignee: UNICHARM CORPORATION, Ehime (JP)

( * ) Notice: Subject to any disclaimer, the term of this patent is extended or adjusted under 35 U.S.C. 154(b) by 279 days.

(21) Appl. No.: 13/515,307

(22) PCT Filed: Dec. 27, 2010

(86) PCT No.: PCT/JP2010/007577
§ 371 (c)(1),
(2), (4) Date: Jun. 12, 2012

(87) PCT Pub. No.: WO2011/080921
PCT Pub. Date: Jul. 7, 2011

(65) Prior Publication Data
US 2012/0253306 A1 Oct. 4, 2012

(30) Foreign Application Priority Data
Dec. 28, 2009 (JP) .................................. 2009-298986

(51) Int. Cl.
*A61F 13/15* (2006.01)
*A61F 13/49* (2006.01)
(Continued)

(52) U.S. Cl.
CPC ... *A61F 13/49058* (2013.01); *A61F 2013/8497* (2013.01); *A61F 13/49012* (2013.01); *A61F 13/539* (2013.01); *A61F 2013/53908* (2013.01)

(58) Field of Classification Search
USPC ............... 604/385.22, 385.24, 385.29, 385.3, 604/383, 378, 379, 380, 366, 367
See application file for complete search history.

(56) References Cited

U.S. PATENT DOCUMENTS

| 5,358,500 A | 10/1994 | Lavon et al. |
| 5,846,232 A | 12/1998 | Serbiak et al. |

(Continued)

FOREIGN PATENT DOCUMENTS

| JP | 2000502268 | 2/2000 |
| JP | 2001061890 | 3/2001 |

(Continued)

OTHER PUBLICATIONS

Supplementary European Search Report issued Oct. 17, 2013, corresponds to European patent application No. 10840780.0.
(Continued)

*Primary Examiner* — Jacqueline Stephens
(74) *Attorney, Agent, or Firm* — Lowe Hauptman & Ham, LLP (57) ABSTRACT

The present invention aims to provide a disposable wearing article improved so that front and rear waist regions may assure desired fitness without adversely affecting an absorption capacity of a bodily fluid-absorbent core assembly. At least one of front and rear waist regions includes an inner sheet lying on a skin-facing side and having stretch properties and an outer sheet lying on a non-skin-facing side and having a low elastic contractile force. In a section of this one waist region occupied by a liquid-absorbent core assembly including a bodily fluid-absorbent core, the inner sheet is partially cut to define a perforated region. Adhesive used to bond the liquid-absorbent core assembly to the inner sheet and adhesive used to bond the inner sheet to the outer sheet are put in contact with and joined to each other through openings developed by partially cutting the inner sheet.

16 Claims, 8 Drawing Sheets (51) Int. Cl.
*A61F 13/539* (2006.01)
*A61F 13/84* (2006.01)

(56) References Cited

U.S. PATENT DOCUMENTS

| | | |
|---|---|---|
| 5,931,827 A | 8/1999 | Buell et al. |
| 6,340,782 B1 | 1/2002 | Kling et al. |
| 2004/0122404 A1 | 6/2004 | Meyer et al. |
| 2004/0209042 A1 | 10/2004 | Peacock |
| 2006/0247591 A1 | 11/2006 | Hughes et al. |
| 2009/0312739 A1 | 12/2009 | Umebayahi et al. |

FOREIGN PATENT DOCUMENTS

| | | |
|---|---|---|
| JP | 2008142315 | 6/2008 |
| WO | 9722318 | 6/1997 |
| WO | 03003961 A1 | 1/2003 |
| WO | 2006118214 | 9/2006 |
| WO | 2009027875 A1 | 3/2009 |

OTHER PUBLICATIONS

International Search Report for PCT/JP2010-007577 mailed Apr. 19, 2011.

DISPOSABLE WEARING ARTICLE

RELATED APPLICATIONS

The present application is a national phase of PCT/JP2010/007577, filed Dec. 27, 2010 and is based on, and claims priority from, Japanese Application Number 2009-298986, filed Dec. 28, 2009.

TECHNICAL FIELD

The present disclosure relates to disposable wearing articles and more particularly to disposable wearing articles such as pant-type disposable diapers, disposable toilet-training pants, disposable incontinent pants, disposable menstruation pants and the like, each having an elastic sheet partially including non-elastic regions.

BACKGROUND

Wearing articles including a waist region elasticized by elastic elements are known. For example, PATENT DOCUMENT 1 (JP 2001-61890 A) discloses a pant-type disposable diaper comprising front and rear waist regions having elasticity and a crotch region.

In the case of the diaper according to the invention disclosed by PATENT DOCUMENT 1 (JP 2001-61890 A), the front and rear waist regions are respectively provided with a plurality of elastic strands extending in a transverse direction of the diaper to assure a desired fit for the respective waist regions. In addition, these elastic strands are cut in a region occupied by a bodily fluid-absorbent core assembly so that substantially no elasticity of the elastic elements can be developed in this region. In this way, the bodily fluid-absorbent core assembly would not be formed with gathers due to contraction of the elastic strands associated with the respective waist regions and, in consequence, a desired liquid-absorption capacity of the bodily fluid-absorbent core assembly would not be adversely affected by the gathers.

However, in the course of partially cutting the elastic elements associated with the waist regions, it is also required to cut an outer sheet cooperating with an inner sheet to sandwich therebetween the bodily fluid-absorbent core assembly. The outer sheet partially cut in this manner may ruin the appearance of the diaper and, if it is desired to provide the outer sheet on its inner surface with graphic displaying film printed with graphics, such graphics might fall apart and be prevented from being visually recognized due to the outer sheet being partially cut.

Therefore, it is desired to provide improved disposable wearing articles so that front and rear waist regions may assure desired fitness without adversely affecting an absorption capacity of a bodily fluid-absorbent core assembly.

CITATION LIST

Patent Literature

[PATENT DOCUMENT 1] JP 2001-61890 A

SUMMARY

The object set forth is achieved, according to one or more embodiments of the present invention, by an improvement in the disposable wearing article having a skin-facing side and a non-skin-facing side and comprising a front waist region, a rear waist region, a crotch region extending between the front and rear waist regions and a bodily fluid-absorbent core extending across the crotch region into the front and rear waist regions.

In this article, at least one of the front and rear waist regions includes an inner sheet lying on the skin-facing side and having stretch properties and an outer sheet lying on the non-skin-facing side and having a low elastic contractile force; in a section of the one of the front and rear waist regions occupied by a liquid-absorbent core assembly including the bodily fluid-absorbent core, the inner sheet is partially cut to define a perforated region; and an adhesive used to bond the liquid-absorbent core assembly to the inner sheet and an adhesive used to bond the inner sheet to the outer sheet are put in contact with and joined to each other through openings developed by the partially cutting the inner sheet.

DETAILED DESCRIPTION

First Embodiment

As shown in FIGS. 1-6, a diaper 10 has a longitudinal direction Y, a transverse direction X orthogonal to the longitudinal direction Y, comprising a skin-facing side and a non-skin-facing side, a chassis 11 defining an outer shape of the diaper 10 and a bodily fluid-absorbent structure 12 lying on the skin-facing side of the chassis 11.

The diaper 10 comprises a front waist region 13, a rear waist region 14 and a crotch region 15 extending between these front and rear waist regions 13, 14, and is contoured by front and rear ends 16, 17 opposed to each other in the longitudinal direction Y and extending in the transverse direction X and side edges 18, 19 opposed to each other in the transverse direction X and extending in the longitudinal direction Y.

The side edges 18, 19 concavely curve in the crotch region 15 to fit about the thighs of the wearer. Opposite side edges 22, 23 of the front waist region 13 are joined to associated opposite side edges 24, 25 of the rear waist region 14 at side seam spots 26 arranged intermittently in the longitudinal direction Y and thereupon a waist-opening 27 and a pair of leg-openings 28 are formed (See FIG. 1).

Figure 1:
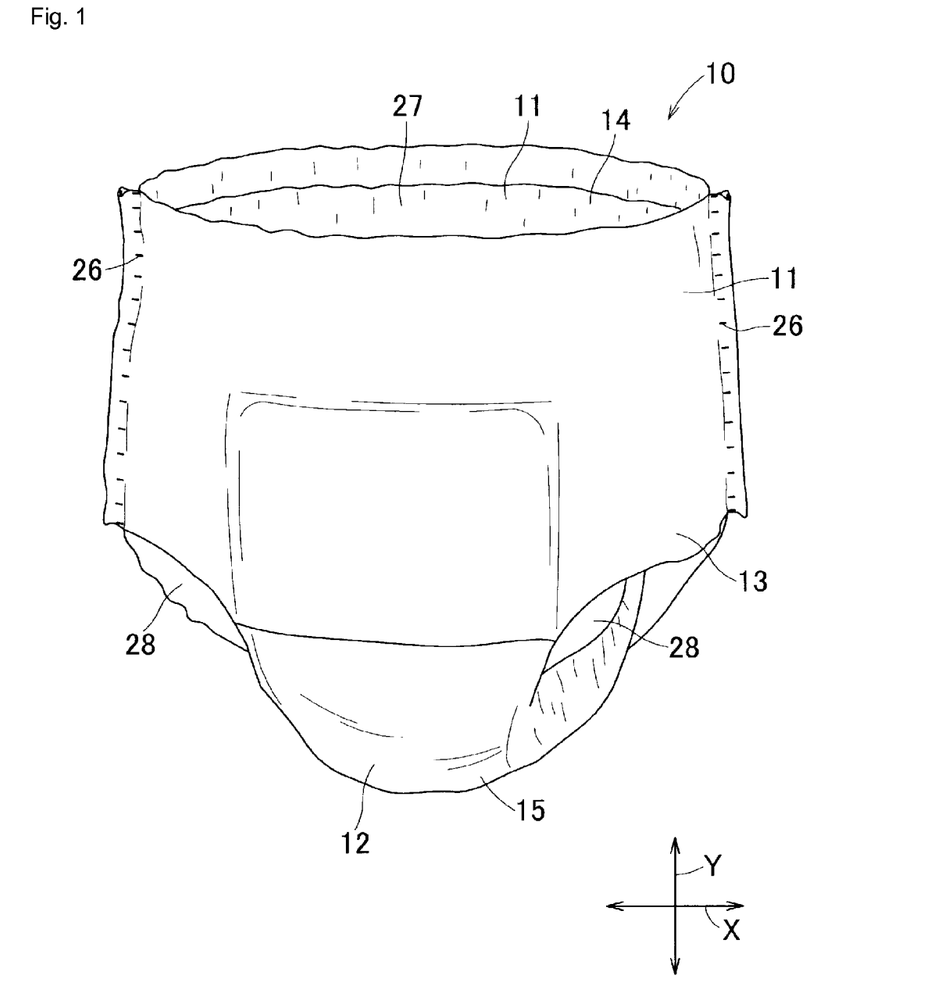
FIG. 1 is a perspective view showing a first embodiment of a disposable diaper as one example of the disposable wearing article according to the first embodiment of the present invention.
Figure 2:
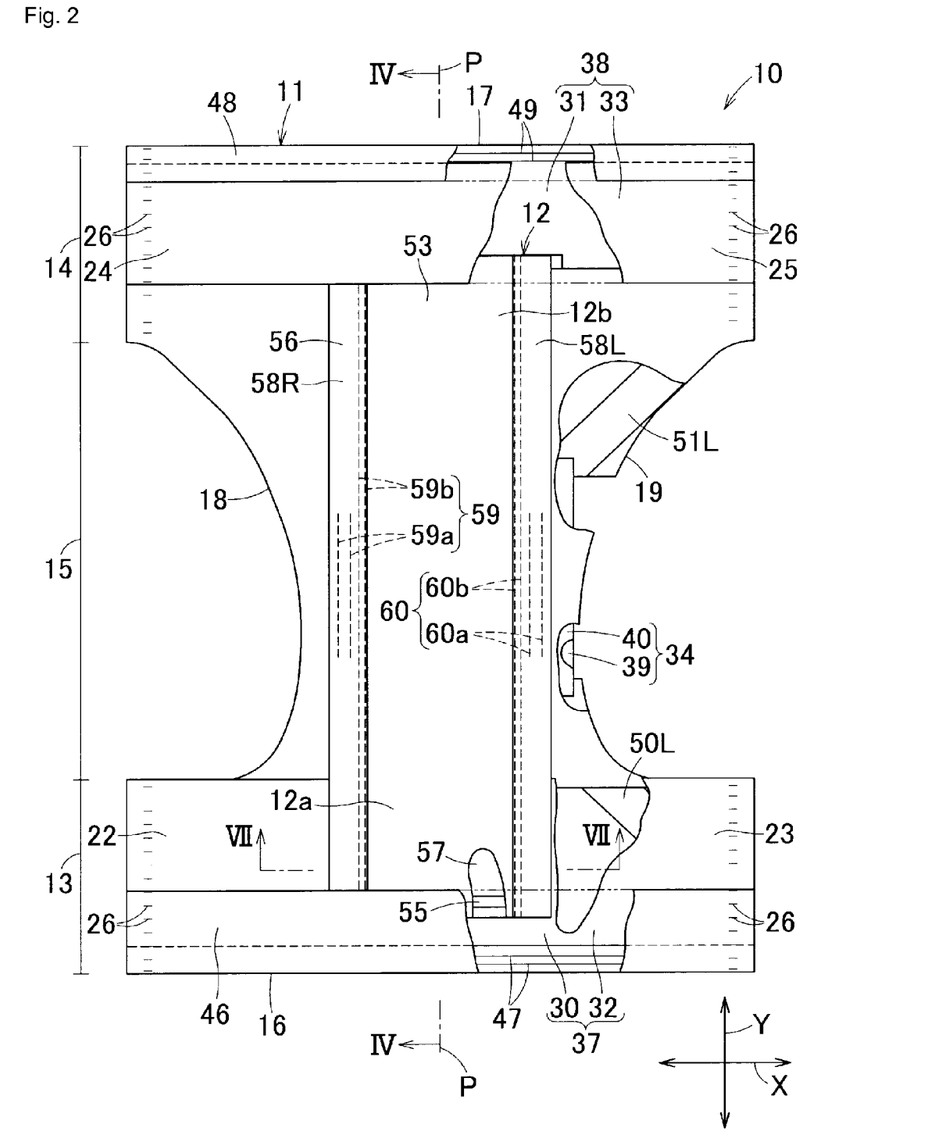
FIG. 2 is a partially cutaway plan view showing the diaper of FIG. 1 in a flatly developed state.
Figure 3:
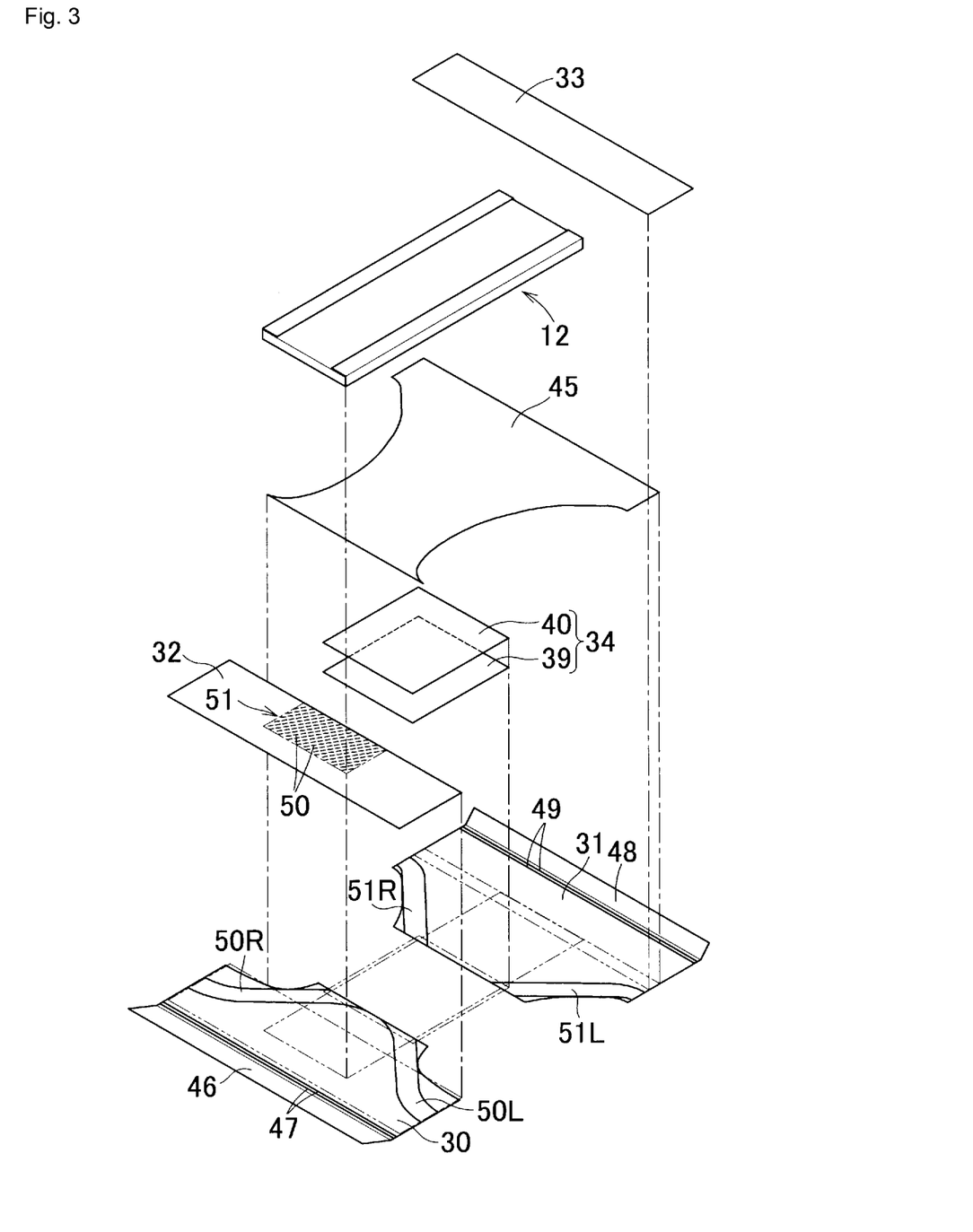
FIG. 3 is an exploded perspective view of the diaper of FIG. 1.
Figure 4:
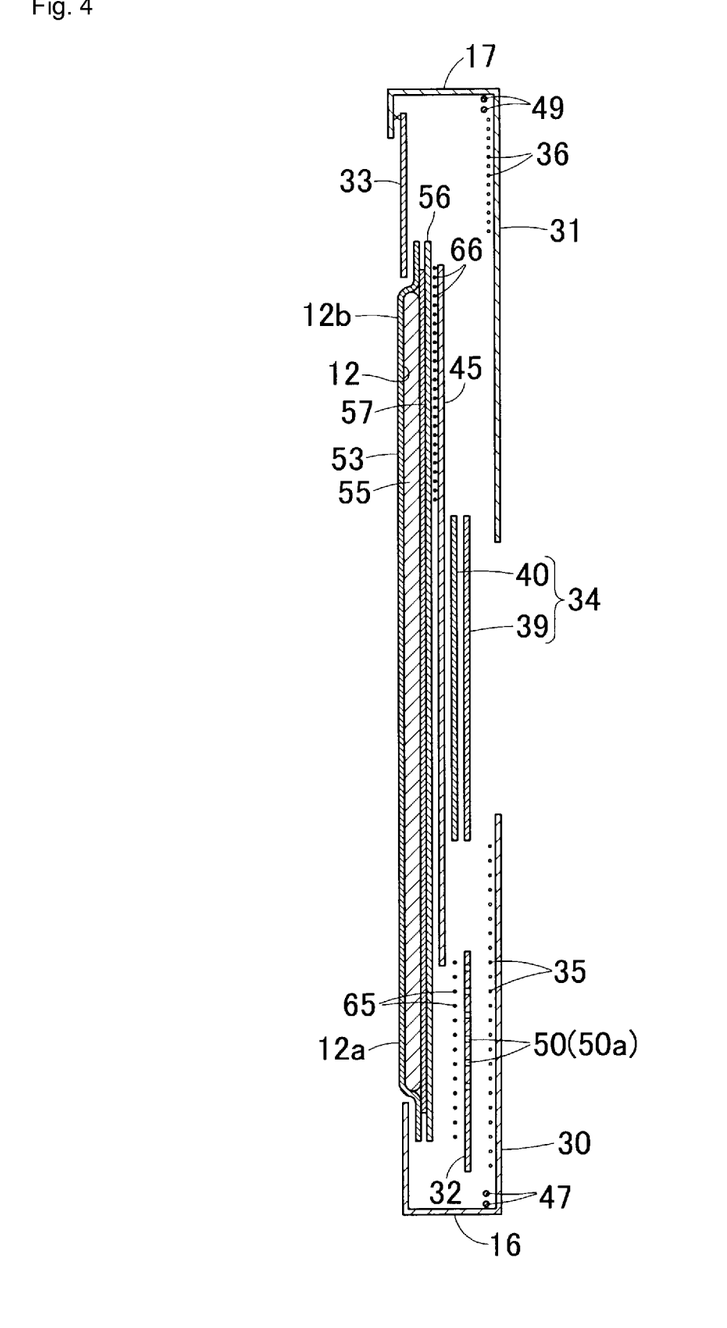
FIG. 4 is a schematic sectional view taken along the line IV-IV in FIG. 2

The chassis 11 includes a generally trapezoidal first outer sheet 30 lying on the non-skin-facing side and defining the front waist region 13 and a part of the crotch region 15, a second outer sheet 31 lying on the non-skin-facing side and defining the rear waist region 14 and a part of the crotch region 15, a first inner sheet 32 lying in the front waist region 13 to extend in the transverse direction X and to be bonded to the skin-facing side of the first outer sheet 30, a second inner sheet 33 lying in the rear waist region 14 to extend in the transverse direction X and to be bonded to the skin-facing side of the second outer sheet 31 and a generally rectangular middle sheet 34 lying between the first and second outer sheets 30, 31 and defining a middle section of the crotch region 15.

The first outer sheet 30 and the first inner sheet 32 are bonded to each other with a first adhesive 35 to form a first laminated sheet 37. The second inner sheet 33 has a width dimension smaller than that of the first inner sheet 32 and is bonded to the second outer sheet 31 with a second adhesive 36 to form a second laminated sheet 38. The middle sheet 34 comprises a generally rectangular fibrous non-woven fabric sheet 39 lying on the non-skin-facing side and a moisture-pervious but liquid-impervious plastic sheet 40 lying on the skin-facing side and being generally the same as the fibrous non-woven fabric sheet 39 in shape as well as in size wherein the fibrous non-woven fabric sheet 39 and the plastic sheet 40 are bonded to each other with hot melt adhesives (not shown) to form the middle sheet 34.

The chassis 11 further includes a fixing sheet 45 made of a fibrous non-woven fabric lying on the skin-facing side and extending across the crotch region 15 into the front and rear waist regions 13, 14. The fixing sheet 45 has a width dimension larger than that of the middle sheet 34 and covers the entire skin-facing surface of the middle sheet 34 provided in the middle section of the crotch region 15.

Along the front end 16 of the front waist region 13, the first outer sheet 30 is folded inward to form a front folded region 46 and, within the front folded region 46, first elastic strands 47 made of an elastomeric material associated with the front waist region 13 are attached under tension in a contractible manner. Similarly, along the rear end 17 of the rear waist region 14, the second outer sheet 31 is folded inward to form a rear folded region 48 and, within the rear folded region 48, second elastic strands 49 made of an elastomeric material associated with the rear waist region 14 are contractibly attached under tension.

A pair of elastic ribbons 50R, 50L are contractibly attached under tension to the inner surface of the first outer sheet 30 to extend from opposite side edges of the front waist region 13 along portions of the crotch region's side edges contiguous to the respective side edges of the front waist region 13 (i.e., front halves of peripheral edges of the respective leg-openings) and to be associated with respective front halves of the leg-openings. Similarly, a pair of elastic ribbons 51R, 51L are contractibly attached under tension to the inner surface of the second outer sheet 31 to extend from opposite side edges of the rear waist region 14 along portions of the crotch region's side edges contiguous to the respective side edges of the rear waist region 14 (i.e., rear halves of peripheral edges of the respective leg-openings) and to be associated with respective rear halves of the leg-openings. The fixing sheet 45 partially covers the elastic elements 50R, 50L associated with the front halves of the leg-openings' peripheral edges and completely covers the elastic elements 51R, 51L associated with the rear halves of the leg-openings' peripheral edges.

The first and second outer sheets 30, 31 are formed of heat sealable spun bonded fibrous non-woven fabrics having generally no elastic stretch properties and having a basis mass in a range of 15 to 40 g/m$^2$, more preferably in a range of 25 to 35 g/m$^2$ and a fiber density in a range of 0.06 to 0.10 g/cm$^3$, more preferably in a range of 0.07 to 0.09 g/cm$^3$. It is possible to form the first and second outer sheets 11, 12 by multiple layers, respectively. In this case, at least the outermost fibrous layer is preferably formed of spun bonded crimped filament fibers to improve flexibility of the diaper 10 as a whole and to assure soft texture. It is also possible to form the first and second outer sheets 30, 31 by fibrous non-woven fabrics having elastic stretch properties lower than that of the first and second inner sheets 32, 33.

The first and second inner sheets 32, 33 are formed of air-through fiber (staple) non-woven fabrics or spun bonded fibrous non-woven fabrics both made of heat sealable elastomeric fibers and having elastic stretch properties. Such fibrous non-woven fabrics have a basis mass in a range of 20 to 50 g/m$^2$, more preferably in a range of 30 to 40 g/m$^2$ and a fiber density in a range of 0.01 to 0.04 g/cm$^3$, more preferably in a range of 0.025 to 0.035 g/cm$^3$.

Figure 5:
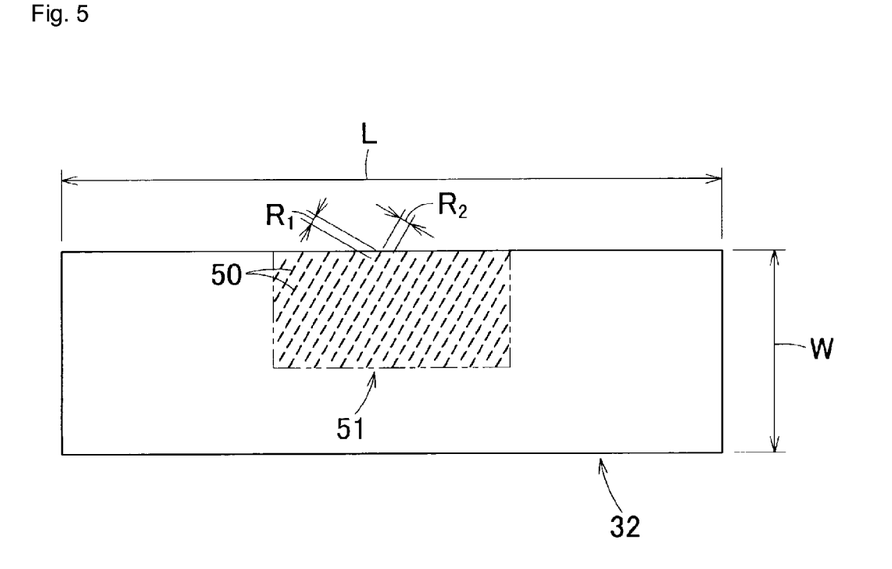
FIG. 5 is a plan view showing a first inner sheet in a non-stretched state.

Now referring to FIG. 5, a middle section of the first inner sheet 32 as viewed in the transverse direction X having its inner surface occupied by a liquid-absorbent core assembly 55 is formed with a plurality of slits 50 each extending obliquely to the longitudinal axis P (at an angle of about 30°) and staggered with respect to the adjacent slits so as to define a perforated region 51 having substantially no elastic stretch properties. With such an arrangement, the first inner sheet 32 develops substantially no elasticity in the region occupied by the liquid-absorbent core assembly 55 and, in consequence, this region is not formed with gathers which would otherwise cause leakage of bodily fluids. In this way, the core assembly can assure its desired liquid-absorption capacity. The first outer sheet 30 neither formed with the slits 50 nor partially cut serves here to prevent the diaper 10 from being disfigured due to the slits of the first inner sheet 32.

Considering the prior art solution in which, instead of the elastic sheets, elastic strands are used to assure a desired fit of the front and rear waist regions 13, 14, these elastic strands must be cut after these elastic strands have been attached to the first outer sheet 30 because it will be extremely difficult in the process of making the diaper 10 to attach them in a partially cut state to the first outer sheet 30. Such handling will inevitably disfigure the diaper 10 and there will be an additional problem that the adhesive used to attach the elastic members to the sheet might be exposed outward through the slits.

Figure 6:
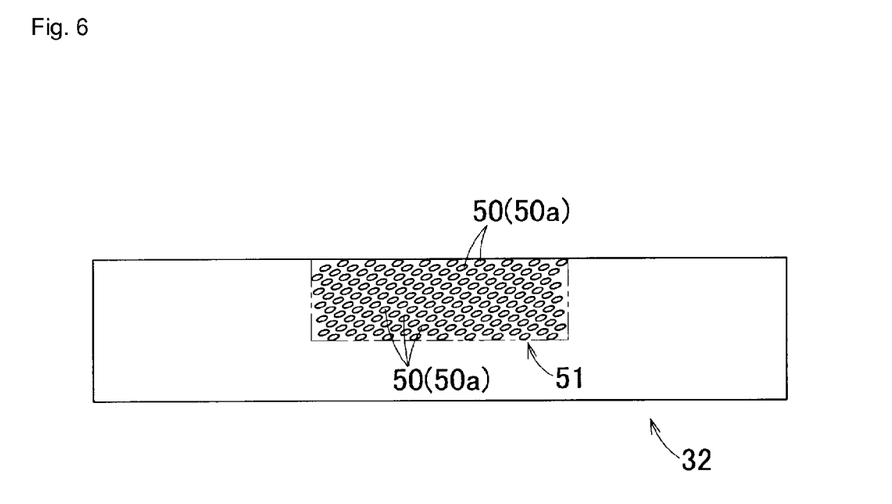
FIG. 6 is a plan view showing the first inner sheet in a stretched state.

Referring to FIG. 6, each of the slits 50 forms a generally elliptical opening 50a as the first inner sheet 32 is stretched in the transverse direction X. In general, it is difficult to form the elastic sheet directly with a plurality of openings and, if it is tried to define the perforation region 51 by a single large opening, continuity as the sheet will be deteriorated and it will be extremely difficult to convey the sheet in the process of making the diaper 10. In contrast, according to this embodiment of the present invention, the first inner sheet 32 is formed with a plurality of the slits 50 and a plurality of the openings 50a are defined by stretching the sheet in the transverse direction X. In this way, it is possible to make the perforated region 51 have substantially low elastic contractile force, to maintain the continuity of the first inner sheet as the sheet and to convey the sheet continuously in the process of making the diaper 10. The arrays of the slits 50 are arranged to extend obliquely to the direction in which the first inner sheet 32 is stretched (i.e., the transverse direction X) so that the individual slits 50 are open as the first inner sheet 32 is stretched. Such an arrangement facilitates a plurality of the openings 50a to be formed without the anxiety that the sheet might be torn from ends of the respective slits even when the sheet is stretched in the transverse direction X.

The expression "a low elastic contractile force" used herein means that the lower elastic contractile force of the first inner sheet 32 is reduced in the perforated region 51 to a level at which the liquid-absorbent core assembly is not formed with gathers or further lower level even when the first inner sheet 32 is stretched in the transverse direction X.

A length dimension R1 of the individual slit 50 and a distance R2 between a pair of adjacent two slits 50 respectively of each pair of the adjacent lines of slits may be appropriately set, depending on a size of the diaper 10 and the preferred dimensions of R1 and R2, to assure that the first inner sheet 32 develops substantially no elastic stretch properties in the perforated region 51 and may be specified on the basis of the conventional diaper of L-size as follows: for the first inner sheet 32 having a width dimension W in the longitudinal direction Y is in a range of about 60 to 120 mm (about 80 mm in the diaper of M-size) and a length dimension L in the transverse direction X is in a range of about 300 to 450 mm (about 340 mm in the diaper of M-size), R1 is in a range of 1.0 to 5.0 mm, R2 is in a range of 8.0 to 10.0 mm and an open area percentage of the openings 50a formed by the slits 50 to the entire area of the perforated region of the first inner sheet 32 is in a range of 10 to 50% (about 20% in the diaper of M-size). It should be appreciated here that the pattern in which the slits 50 are arranged is not limited to the staggered pattern and the slits 50 may be arranged in the various well known patterns other than the staggered pattern so far as the effect of the present invention can be obtained. The shape of the opening 50a formed by the individual slit 50 also is not limited to the elliptical shape but the may be in the other shape such as circular or square shape. It is possible to form the perforated region 51 comprising the slits 50 not only in the first inner sheet 32 but also in the second inner sheet 33.

Both the middle sheet 34 and the fixing sheet 45 may be formed of spun bonded fibrous non-woven fabrics partially containing crimped fibers as in the case of the first and second outer sheets 30, 31 or by elastically non-stretchable air-through fibrous non-woven fabrics or the like.

Referring to FIG. 2, a liquid-absorbent structure 12 has a rectangular shape which is longer in the longitudinal direction Y than in the transverse direction X and contoured by a front end 12a lying in the front waist region 13, a rear end 12b lying in the rear waist region 14 and opposite side edges extending orthogonally to these front and rear ends 12a, 12b to extend across the crotch region 15 into the front and rear waist regions 13, 14. More specifically, the liquid-absorbent structure 12 comprises a liquid-pervious top-sheet 53 lying on the skin-facing side, the liquid-absorbent core assembly 55 formed of a mixture, for example, of fluff pulp fibers and super-absorbent polymer particles wrapped with a liquid-dispersant sheet (not shown), a cover sheet 56 lying on the non-skin-facing side to cover the liquid-absorbent core assembly 55 as a whole and a leakage-barrier sheet 57 made of a plastic material and sandwiched between the liquid-absorbent core assembly 55 and the cover sheet 56.

The cover sheet 56 has opposite lateral sections extending outward in the transverse direction X from the side edges of the liquid-absorbent core assembly 55. The lateral sections are partially folded inward to form a pair of sleeve-like side flaps 58L, 58R extending in the longitudinal direction Y and, within the respective side flaps 58L, 58R, four elastic strands 59, 60 made of an elastomeric material and extending in the longitudinal direction Y are contractibly attached under tension to these side flaps by hot melt adhesives. Of respective four elastic strands 59, 60, respective outer two elastic strands 59a, 60a are located in the middle section of the crotch region 15 and cooperate with the first and second elastic ribbons 50R, 50L, 51R, 51L to define elastic belts extending along the wearer's inguinal regions. Of respective four elastic strands 59, 60, respective inner two elastic strands 59b, 60b extend within the respective side flaps 58R, 58L across the crotch region 15 into the front and rear waist regions 13, 14. Opposite lateral sections of the cover sheet 56 are spaced from the top-sheet 53 under contraction of the elastic strands 59, 60 to form barrier- or gasket-cuffs adapted to prevent body waste from leaking sideways.

The liquid-absorbent structure 12 has its front end 12a attached to the inner surface of the first inner sheet 32 with a third adhesive 65 applied to the outer surface of the front end 12a and the rear end 12b attached to the inner surface of the fixing sheet 45 with of a fourth adhesive 66 applied to the outer surface of the rear end 12b.

It is possible to provide the first and second inner sheets 32, 33 to extend from respective inner boundaries of the front and rear waist regions 13, 14 into the crotch region 15. Instead of providing the fixing sheet 45 on the skin-facing side, it is possible to form the chassis 11 as a whole only by outer and inner sheets each defining the outer shape of the diaper 10 so that the diaper 10 as a whole may have elastic stretch properties. It is also possible to use the second inner and outer sheets 31, 33 configured in the same manner as the above-described first inner and outer sheets 30, 32.

Figure 7:
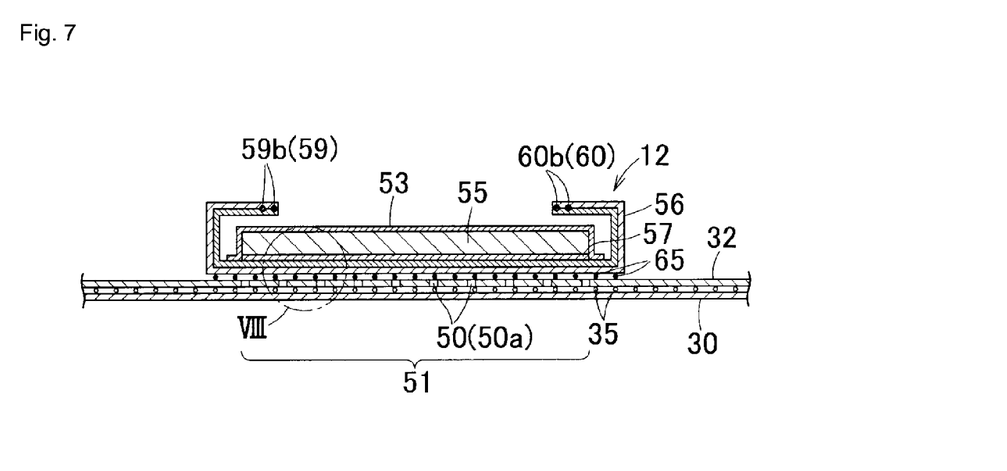
FIG. 7 is a sectional view taken along the line VII-VII in FIG. 2.
Figure 8:
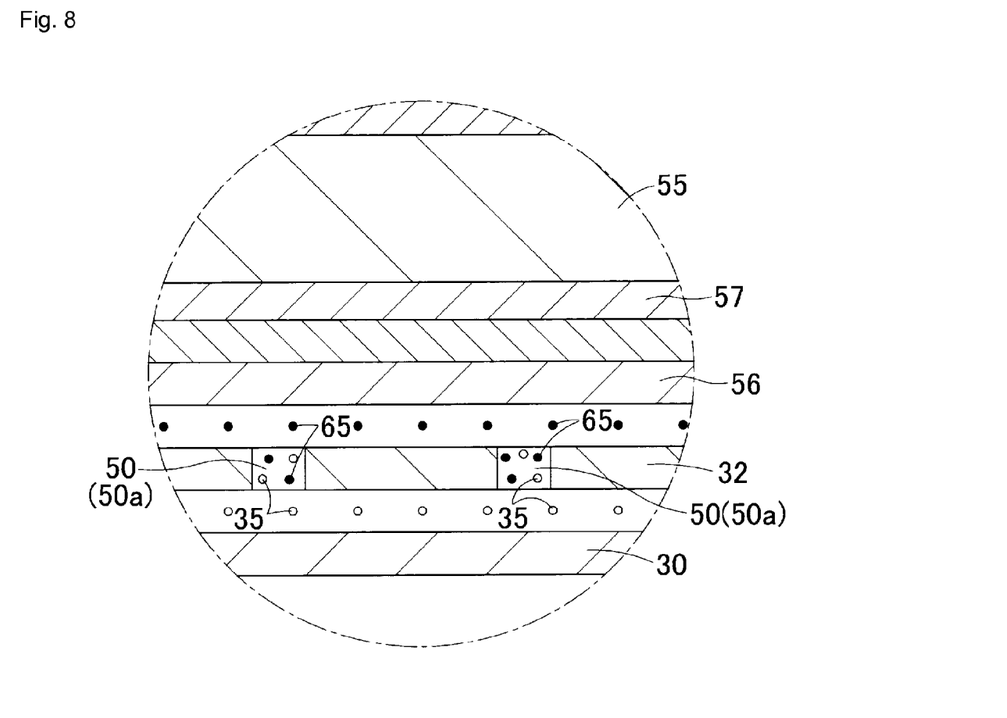
FIG. 8 is a partially scale-enlarged diagram illustrating the region VIII indicated by dashed-dotted line in FIG. 7.

As will be apparent from FIG. 7, the perforated region 51 defined in the first inner sheet 32 allows the first adhesive 35 and the third adhesive 65 to come in contact and join together through the openings 50a as the respective slits 50 are opened. The first adhesive 35 and the third adhesive 65 put in contact with and joined together in this manner surely fix the regions defined between each pair of the adjacent slits 50 so that the elastic stretch properties of these regions may be restricted and thereby undesirable twist of the first inner sheet 32 in the perforated region 51 which would otherwise be developed due to the elastic stretch properties of the first inner sheet 32 in the region other than the perforated region 51 may be reliably prevented.

While various types of well known adhesives can be selectively used as the first through fourth adhesives 35, 36, 65, 66, rubber-based adhesives, for example, SBS (styrene-butadiene-styrene)-based or SIS (styrene-isoprene-styrene)-based hot melt adhesives having a basis mass in a range of 1.0 to 2.5 g/m$^2$ may be preferably used to protect the stretch properties of the first and second elastic sheets 51, 52 in the regions other than the perforated region 51 from any adverse affection of these hot melt adhesives as reliably as possible. The first through fourth adhesives 35, 36, 65, 66 may be applied in various well known patterns such as an omega-pattern, a spiral pattern, a dotted pattern, a wavy pattern and a reticular pattern. When an omega-pattern is employed, the adhesive line's diameter is preferably in a range of 0.01 to 0.1 mm and more preferably in a range of 0.03 to 0.07 mm. A distance dimension between each pair of the adjacent adhesive lines is preferably in a range of 1.0 to 2.5 mm and more preferably in a range of 1.5 to 2.0 mm. An area percentage of the adhesive lines to the total inner surface area of the first and second inner sheets 32, 33 is preferably in a range of 2 to 10% and more preferably in a range of 4 to 6%.

Second Embodiment

Figure 9:
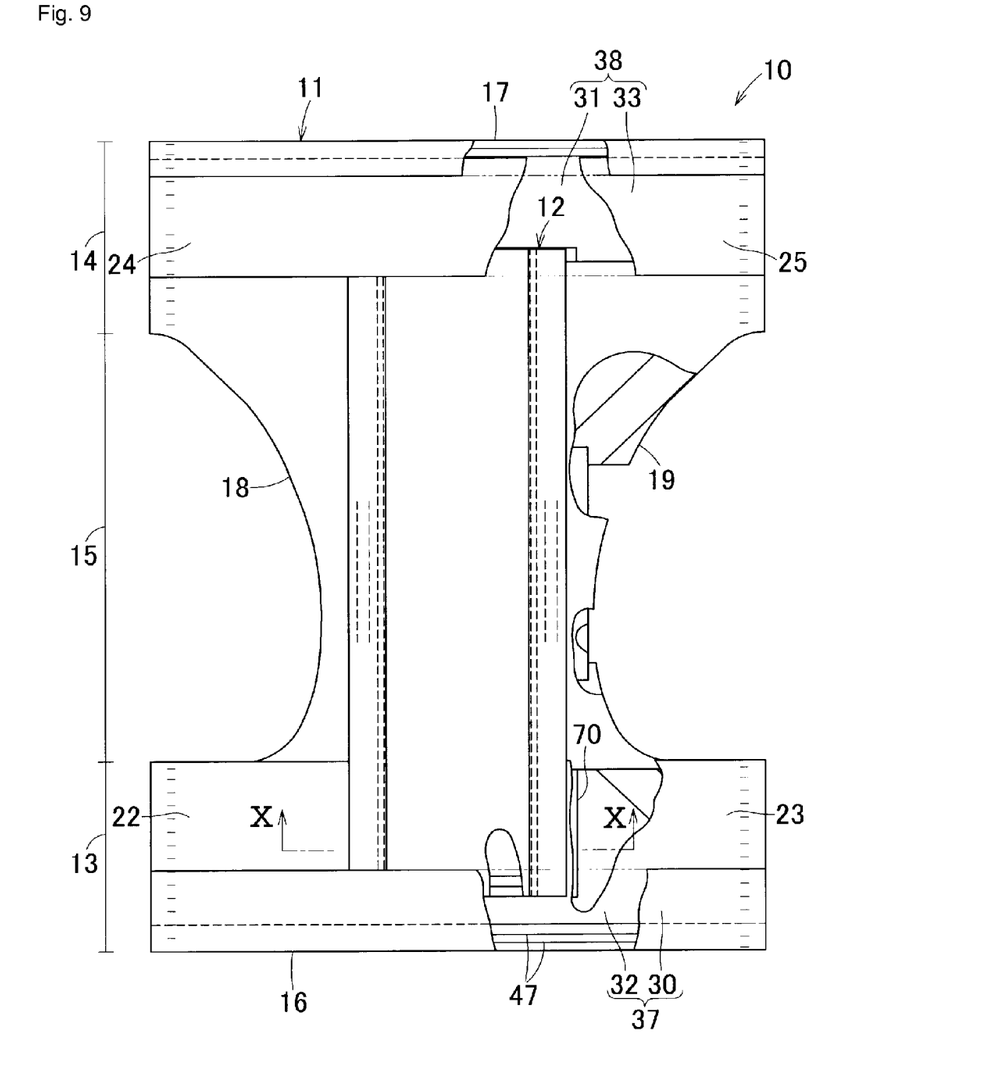
FIG. 9 is a plan view showing a diaper as a second embodiment of the present invention in a flatly developed state.
Figure 10:
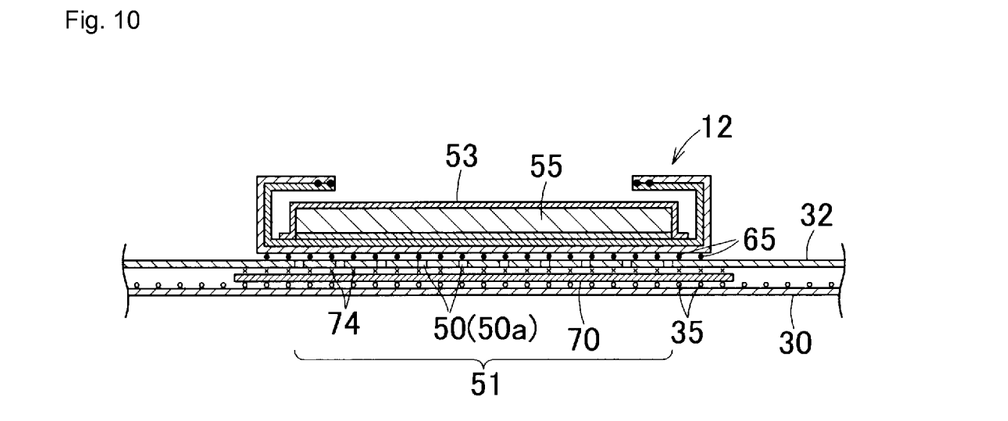
FIG. 10 is a sectional view taken along the line X-X in FIG. 9.

According to the second embodiment as shown in FIGS. 9 and 10, a middle section of the front waist region 13 as viewed in the transverse direction X is provided with graphic displaying film 70 made of a plastic material and printed with a graphics (not shown) adapted to be visually recognized from the outside. In the front waist region 13, this graphic displaying film 70 is fixed to the inner surface of the first outer sheet 30 with the first adhesive 35 and fixed to the first inner sheet 32 with a fifth adhesive 74. The fifth adhesive 74 is put in contact with and joined to the third adhesive 65 through the openings formed by the respective slits 50 so that the elastic stretch properties of the first inner sheet 32 may be restricted in the perforated region 51 and, at the same time, the graphic displaying film 70 may be reliably fixed between the first outer sheet 30 and the first inner sheet 32 without any displacement. The graphic displaying film 70 is formed with none of the slits 50 and, in consequence, the graphics would not get out of shape and the initial visibility would not be disturbed.

While the rear waist region 14 has been described above to be arranged in a manner different from the front waist region 13, it is possible to use the rear waist region having the same configuration as the front waist region 13 according to the first and second embodiments. As stock materials for the respective components of the diaper 10 according to the present invention, various well known stock materials conventionally used in the relevant technical field may be selectively used unless otherwise specified. Instead of forming the front and rear waist regions 13, 14 of separate sheet members, it is possible to form the front and rear waist regions 13, 14 and the crotch region 15 in an integrated fashion. More specifically, each of the inner and outer sheets 30, 31, 32, 33 may be a single sheet having a concave shape curved inwardly corresponding to the outer shape of the diaper 10.

The aspects of the present invention described above may be arranged in at least following items:

(i) A disposable wearing article (10) having a skin-facing side and a non-skin-facing side, comprising a front waist region (13), a rear waist region (14), a crotch region (15) extending between the front and rear waist regions and a bodily fluid-absorbent core (55) extending across the crotch region into the front and rear waist regions, wherein:

at least one of the front and rear waist regions includes an inner sheet (32) lying on the skin-facing side and having stretch properties and an outer sheet (30) lying on the non-skin-facing side and having a low elastic contractile force;

in a section of the one of the front and rear waist regions occupied by a liquid-absorbent core assembly including the bodily fluid-absorbent core, the inner sheet is partially cut to define a perforated region (51); and an adhesive (65) used to bond the liquid-absorbent core assembly to the inner sheet and an adhesive (35) used to bond the inner sheet to the outer sheet are put in contact with and joined to each other through openings (50a) developed by the partially cutting the inner sheet.

The aspect of the present invention described in the above item (i) may provide one or more of the following advantageous effects: (a) since the inner sheet having stretch properties is located on the skin-facing side to assure an agreeable fit of the waist region and the section of the inner sheet occupied by the bodily fluid-absorbent core assembly including the bodily fluid-absorbent core is partially cut to define the perforated region generally having low elastic contractile force, the absorption capacity of the bodily fluid-absorbent core assembly may be free from any adverse affection by the stretch properties of the inner sheet. The outer sheet lying on the non-skin-facing side is not partially cut and therefore the diaper would not be disfigured.

Additionally, one or more of the following embodiments, which may be taken in isolation or in combination, may be provided in accordance with further aspects:

The perforated region may be defined by a plurality of slits arranged in the perforated region of the inner sheet.

The slits may be arranged at an oblique angle to a transverse axis of the wearing article.

The slits may be arranged at an angle of 30 degrees to a transverse axis of the wearing article.

The slits may be arranged in lines with all of the slits in each line axially aligned with one another.

Adjacent lines of slits may be spaced from one another by 8 to 10 mm.

The slits may have a length of 1 to 5 mm.

The inner sheet may be bonded to the liquid absorbent core and to the outer sheet in a transversely stretched state. In other words the inner sheet is bonded under tension in the transverse direction.

The openings may be arranged to be formed by stretching the inner sheet in the transverse direction.

Preferably, the entire region of said one of said front and rear waist regions that is occupied by the liquid-absorbent core assembly is covered with openings.

An open area percentage of the openings to the entire region of said one of said front and rear waist regions that is occupied by the liquid-absorbent core assembly may be in a range of 10 to 50%.

Preferably, both of said front and rear sections include an inner sheet.

A plastic film (70) may be sandwiched between the inner sheet and the outer sheet and wherein the adhesive used to bond the liquid-absorbent core assembly to the inner sheet and adhesive used to bond the inner sheet to the plastic film are put in contact with and joined to each other through the openings.

The plastic film may define a graphic displaying film printed with graphics adapted to be visually recognized from the outside.

According to the embodiments in the above paragraphs, the advantageous effect(s) set forth at (a) may be better ensured. Further advantageous effects of the respective embodiments may be obtained as discussed in the respective related descriptions.

The invention claimed is:

1. A disposable wearing article comprising a skin-facing side, a non-skin-facing side, a front waist region, a rear waist region, a crotch region extending between said front and rear waist regions and a liquid-absorbent core assembly extending across said crotch region into said front and rear waist regions, wherein:

at least one of said front and rear waist regions includes an inner sheet lying on said skin-facing side and having stretch properties, and an outer sheet lying on said non-skin-facing side and having a low elastic contractile force;

in a section of said one of said front and rear waist regions occupied by the liquid-absorbent core assembly, said inner sheet is partially cut to define a perforated region; and an adhesive bonding said liquid-absorbent core assembly to said inner sheet and an adhesive bonding said inner sheet to said outer sheet are put in contact with and joined to each other through openings developed by said partially cutting said inner sheet.

2. The wearing article defined by claim 1, wherein said perforated region is defined by a plurality of slits.

3. The wearing article defined by claim 2, wherein the slits are arranged at an oblique angle to a transverse axis of the wearing article.

4. The wearing article defined by claim 2, wherein the slits are arranged at an angle of 30 degrees to a transverse axis of the wearing article.

5. The wearing article defined by claim 2, wherein the slits are arranged in lines with all of the slits in each line axially aligned with one another.

6. The wearing article defined by claim 5, wherein adjacent lines of slits are spaced from one another by 8 to 10 mm.

7. The wearing article defined by claim 2, wherein the slits have a length of 1 to 5 mm.

8. The wearing article defined by claim 2, wherein the inner sheet is bonded to the liquid absorbent core and to the outer sheet in a transversely stretched state.

9. The wearing article defined by claim 8, wherein the inner sheet is stretched in a transverse direction of the wearing article to define the openings.

10. The wearing article defined by claim 1, wherein the entire section of said one of said front and rear waist regions that is occupied by the liquid-absorbent core assembly is covered with the openings.

11. The wearing article defined by claim 1, wherein an open area percentage of the openings to the entire region of said one of said front and rear waist regions that is occupied by the liquid-absorbent core assembly is in a range of 10 to 50%.

12. The wearing article defined by claim 1, wherein both of said front and rear waist regions each include an inner sheet.

13. The wearing article defined by claim 1, further comprising a plastic film sandwiched between said inner sheet and said outer sheet, wherein said adhesive bonding said liquid-absorbent core assembly to said inner sheet and an adhesive bonding said inner sheet to said plastic film are put in contact with and joined to each other through said openings.

14. The wearing article defined by claim 13, wherein said plastic film defines a graphic displaying film printed with graphics visible from the outside of the wearing article.

15. The wearing article defined by claim 1, wherein said perforated region has a contractile force lower than that of a non-perforated region of the inner sheet.

16. The wearing article defined by claim 1, wherein some of the adhesive bonding said liquid-absorbent core assembly to said inner sheet and some of the adhesive bonding said inner sheet to said outer sheet are mixed with each other in some of the openings of the inner sheet.

* * * * *